United States Patent [19]

Macdonell

[11] 4,256,903

[45] Mar. 17, 1981

[54] POLYMER INHIBITION

[75] Inventor: Gary D. Macdonell, Bartlesville, Okla.

[73] Assignee: Phillips Petroleum Company, Bartlesville, Okla.

[21] Appl. No.: 130,677

[22] Filed: Mar. 17, 1980

[51] Int. Cl.$^3$ .................................................. C07D 333/48
[52] U.S. Cl. ............................................................ 549/87
[58] Field of Search .............................................. 549/87

[56] References Cited

U.S. PATENT DOCUMENTS

| 3,514,469 | 5/1970 | Phillips et al. | 549/87 |
| 3,544,430 | 12/1970 | Mihm | 549/87 |

Primary Examiner—Alan Siegel

[57] ABSTRACT

The formation of polysulfone polymer during the synthesis of sulfolenes from conjugated dienes and sulfur dioxide is reduced by the incorporation of a small, effective amount of a mono- and/or dialkenyl amine.

8 Claims, No Drawings

POLYMER INHIBITION

This invention relates to the preparation of sulfolenes. In accordance with another aspect, this invention relates to the inhibition of polymer formation during the synthesis of sulfolenes by the addition of a polymerization inhibitor. In accordance with another aspect, this invention relates to the synthesis of sulfolenes from conjugated dienes and sulfur dioxide in the presence of a dialkenyl amine polymerization inhibitor. In accordance with a further aspect, this invention relates to the use of mono- and/or dialkenyl amines as inhibitors in reducing the amount of polysulfone polymer formed during the synthesis of sulfolenes.

BACKGROUND OF THE INVENTION

Sulfolene compounds are generally used as intermediates for the corresponding hydrogenated sulfolane derivatives which are in turn useful as selective solvents, ingredients in pesticidal compositions, and intermediates for other organic chemicals. Sulfolenes are unsaturated five-membered rings of four carbon atoms and a sulfur atom, the latter having two oxygen atoms directly attached thereto. Thus, the generic term "sulfolene" covers the simple unsubstituted sulfolenes, viz., the 2-sulfolene and the 3-sulfolene having the general structures

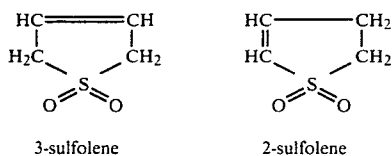

3-sulfolene      2-sulfolene as well as the various substituted derivatives described herein. Sulfolenes are generally prepared by reacting sulfur dioxde with a conjugated diene like 1,3-butadiene. In addition, polymerization inhibitors are sometimes added to reduce the undesirable formation of polysulfone polymers. One such method is described in U.S. Pat. No. 3,514,469 which employs substituted phenols like pyrogallol, tert-butyl pyrocatechol and such amines as phenyl-β-naphthylamine as polymer inhibitors in the synthesis of sulfolene. Thus, the essence of the current invention is to provide an alternate class of compounds, namely the mono- and dialkenyl amines, as inhibitors to reduce the formation of polysulfone polymers in the preparation of sulfolenes. It has also been found that these alkenyl amines do not interfere with subsequent reactions such as hydrogenation which converts the sulfolenes to sulfolanes.

Accordingly, an object of this invention is to provide an improved process for the production of sulfolene compounds.

It is another object of this invention to provide a polymerization inhibitor useful in the synthesis of sulfolenes.

Another object of this invention is to provide a process whereby polymer formation is minimized during the synthesis of sulfolenes.

Other objects, aspects, and the several advantages of this invention will become apparent to one skilled in the art upon reading this disclosure and the appended claims.

SUMMARY OF THE INVENTION

In accordance with the invention, a process is provided for the production of sulfolenes which comprises reacting $SO_2$ and a conjugated diene in the presence of a finite, small, but effective amount, sufficient to inhibit and minimize polymer formation, of an alkenyl amine.

In accordance with one embodiment of the invention, the formation of polysulfone polymer during the synthesis of sulfolenes from conjugated dienes and sulfur dioxide is reduced by the incorporation of a polymerization inhibitor comprising mono- and/or dialkenyl amines.

In accordance with a specific embodiment, sulfolene is produced from butadiene and sulfur dioxide in the presence of diallylamine to reduce the amount of polysulfone polymer formed.

DETAILED DESCRIPTION OF THE INVENTION

Sulfolene Precursors

The sulfolene compounds can be prepared by reacting sulfur dioxide with a conjugated diene having the structural formula

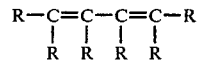

wherein each R is selected from the group consisting of hydrogen and various organic and/or inorganic radicals which do not interfere with the reaction to produce the sulfolene compound or the subsequent hydrogenation reaction to produce the corresponding sulfolane compound. Inorganic radicals which are suitable include the halogens, hydroxyl groups, and the like. Organic radicals which are preferred include hydrocarbyl substituents having up to and including 8 carbon atoms per radical. A presently preferred class of starting materials comprises the conjugated diolefins of the structural formula indicated where each R is individually selected from the group consisting of hydrogen, alkyl, alkenyl, aryl, cycloalkyl, and cycloalkenyl and combinations thereof such as aralkyl, alkaryl, and alkylcycloalkyl, where the total carbon content of the molecule is in the range of 4 to 12. Representative examples of the unsaturated organic compound include, but are not limited to, for example, 1,3-butadiene, 2-methyl-1,3-butadiene (isoprene), 2,3-dimethyl-1,3-butadiene, 2,3-diethyl-1,3-butadiene, 3,4-dimethyl-2,4-hexadiene, 2,4-dodecadiene, 2-methyl-1,3-hexadiene, 4-ethyl-1,3-hexadiene, 1-cyclopentyl-1,3-pentadiene, 1-(1-cyclohexene-1-yl)-1,3-butadiene, 2-phenyl-1,3-butadiene, 3-benzyl-1,3-pentadiene, 3-p-tolyl-1,3-pentadiene, and the like, and their homologues and analogues. Also, suitable substituted derivatives of the above and like polyenes may be reacted with sulfur dioxide to form the desired mono-sulfones, examples of such substituted polyenes being 2-chloro-1,3-butadiene, 2-methyl-3-chloro-1,3-butadiene, 1-cyano-1,3-butadiene, and the like, and admixtures thereof.

The instant invention is applicable to systems wherein the sulfolene feed is produced initially in the presence of a solvent or wherein the sulfur dioxide is reacted with a sulfolene precursor in the absence of a solvent to produce a molten sulfolene compound which is thereafter introduced into a suitable hydrogenation solvent.

Sulfolenes

Sulfolenes prepared according to the invention are those materials having either general structural formula

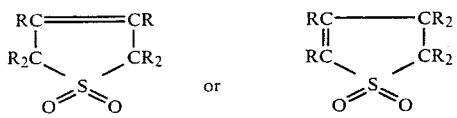

wherein each R is individually selected as herein described. The following representative sulfolene compounds are among those prepared according to the current invention: 2-sulfolene, 3-sulfolene, 3-methyl-2-sulfolene, 2-methyl-3-sulfolene, 3-methyl-3-sulfolene, 2,4-dimethyl-2-sulfolene, 2,4-dimethyl-3-sulfolene, 3-ethyl-3-sulfolene, and their homologues, as well as other sulfolene compounds, and admixtures thereof.

Alkenyl Amine Inhibitor

Alkenyl amines useful as polysulfone polymer inhibitors in this invention are represented by the formula

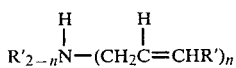

wherein n equals 1 or 2 and R' can be hydrogen or any hydrocarbyl radical having from 1 to 6 carbon atoms. Typical alkenyl amine compounds are, for example, but not limited to such materials as allylamine, methylallylamine, ethylallylamine, butylallylamine, hexylallylamine, cyclohexylallylamine, diallylamine, 2-butenylamine, methyl 2-butenylamine, di(2-butenyl)amine, 2-pentenylamine, di(2-pentenyl)amine, 2-hexenylamine, hexyl 2-hexenylamine, di(2-hexenyl)amine, 2-nonenylamine, di(2-nonenyl)amine, and the like, and mixtures thereof.

The amount of mono- or dialkenyl amines useful as polysulfone polymer inhibitors in the preparation of sulfolene is a small but effective amount which is sufficient to inhibit and minimize formation of polymer. In general, the amounts of inhibitor present will range broadly from about 0.01 to about 10 wt. % and preferably about 0.1 to about 5 wt. % based on the weight of the conjugated diene employed.

The sulfolene compounds can be prepared by reacting sulfur dioxide with at least one sulfolene precursor compound (conjugated diene) as defined herein to produce the sulfolene compound for the subsequent hydrogenation reaction to produce the corresponding sulfolane compound.

The conditions utilized for producing sulfolene compounds are well known in the art as exemplified in U.S. Pat. No. 3,622,598, James L. Willis, issued Nov. 23, 1971, which is incorporated herein by reference. Representative examples of suitable conditions include: sulfur dioxide:conjugated diene mol ratios of from 1:1 to about 1.6:1, reaction temperature of from about 37° C. (100° F.) to about 149° C. (300° F.), and reaction pressures of from about 100 psig to about 600 psig.

The sulfolene reaction mixture obtained can be separated into sulfolene and other components, if desired, or subjected directly to hydrogenation to convert sulfolene to sulfolane. The term "sulfolane" as employed herein refers to a saturated sulfolane compound which can be either substituted or unsubstituted. The sulfolane compound contains or consists of a saturated 5-membered ring of four carbon atoms and a sulfur atom, the latter having two oxygen atoms directly attached thereto. The structural formula of the simple unsubstituted sulfolane, therefore, is

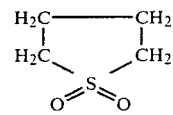

Hydrogenation of the sulfolene compounds, produced according to the invention, with the minimimum amount of polymer formation can be accomplished in the presence of known hydrogenation catalysts as set forth in U.S. Pat. No. 3,514,469, which is incorporated herein by reference.

The following examples serve to illustrate the operability of the current invention.

EXAMPLE I

This example is a control which illustrates the effect saturated dialkyl amines have on the amount of polysulfone polymer formed from the reaction of $SO_2$ and butadiene to give 3-sulfolene. To a 1-liter stainless steel reactor was charged 7 milliliters (4.8 grams) dimethylamine and 294 grams (4.59 moles) of $SO_2$. The reaction mixture was warmed to 69°–72° C. (156°–161° F.) and 216 grams (3.99 moles) of butadiene was pumped in at a rate of about 4 milliliters per minute while maintaining operating temperature by circulating water through internal cooling coils. The pressure during the butadiene addition was about 200 psig (1378 kPa) which slowly decreased to 150 psig (1034 kPa) by the end of the butadiene addition (e.g., 1.5 hours). The reaction mixture was kept at 70° C. with stirring for 6 hours while the pressure slowly decreased to about 70 psig (482 kPa). Afterwards the reaction was allowed to cool to ambient room temperature overnight. Excess $SO_2$ was vented and 300 milliliters of water was added. The reaction mixture was warmed to 45° C. (113° F.), drained from the reactor and filtered hot to remove unwanted polysulfone polymer. The filtrate was cooled at about 5° C. overnight and the solid sulfolene product that precipitated was filtered and air-dried to give a 72 mole % yield (340 grams) of 3-sulfolene. The polymer originally separated was air dried to give 9.93 grams (2.10 wt. % water insolubles based on the theoretical amount of 3-sulfolene expected, namely 471.4 grams). The polymer analyzed as: %C, 40.92; %H, 5.16; %S, 26.72; %O, 27.0. Analysis for sulfolene, $C_4H_6SO_2$, is calculated to be %C, 40.6; %H, 5.1; %S, 27.1; %O, 27.1. The experiment was repeated whereupon 8.13 grams (1.72 wt. %) of polymer was obtained.

Repeating the run with more dimethylamine present (7.2 grams) gave less polymer, 4.88 grams (1.03 wt. % water insolubles). Again repeating the run with still more dimethylamine present (9.6 grams) gave still less polymer, 1.64 grams (0.35 wt. % water insolubles).

EXAMPLE II

This example is a control which illustrates the effect other type amines have on the inhibition of polysulfone polymer formation during 3-sulfolene synthesis. Six amines of various cyclic structure were tested. None of these were found to be significantly better than the dimethylamine employed in Example I. Moreover, those amines which were about equally as effective as dimethylamine in inhibiting polymer formation imparted more color to the sulfolene product, thus, rendering them unsatisfactory. The additional amines tested are listed in Table I.

TABLE I

Amines as Polymer Inhibitors in 3-Sulfolene Synthesis
charge: 216 grams (3.99 moles) butadiene
294 grams (4.59 moles) SO$_2$

| Inhibitor (4.4 Wt. %)$^a$ | Wt. % Polymer Formed$^b$ | Sulfolene Color |
|---|---|---|
| 1. Dimethylamine | 0.35$^c$ | Light yellow |
| 2. Diphenylamine | 0.32 | Dark brown |
| 3. Piperidine | 0.33 | Light green |
| 4. Morpholine | 0.55 | Green |
| 5. Dicyclohexylamine | 0.92 | Light brown |
| 6. 2,2,6,6-tetramethylpiperidine | 1.07 | Light green |
| 7. N-Methylpiperazine | 15.47 | Water white |

$^a$Based on butadiene charged.
$^b$Based on theoretical amount of sulfolene formed.
$^c$Average of 2 values.

EXAMPLE III

This example illustrates the current invention wherein dialkenyl amines are employed as polymer formation inhibitors in the synthesis of 3-sulfolene from SO$_2$ and butadiene. The run described in Example I was repeated except diallylamine was used as a polymer formation inhibitor in place of dimethylamine. The results which are listed in Table II show that at equal concentration, diallylamine is a better polymer formation inhibitor than dimethylamine. In addition, the product 3-sulfolene is generally less colored. The results from Example I employing dimethylamine are listed for comparison.

TABLE II

Diallylamine as Polymer Inhibitor in 3-Sulfolene Synthesis

| Inhibitor Name | Wt. % Used$^a$ | Wt. % Polymer Formed$^b$ | 3-Sulfolene Color |
|---|---|---|---|
| 1. Dimethylamine | 2.2 | 1.91$^c$ | light green to yellow |
|  | 3.3 | 1.03 | water white |
|  | 4.4 | 0.37$^d$ | light yellow to water white |
| 2. Diallylamine | 2.2 | 0.46$^d$ | water white to light yellow |
|  | 3.3 | 0.25$^c$ | water white to light green |
|  | 4.4 | 0.18$^c$ | water white to light green |

$^a$Based on weight of butadiene used.
$^b$Based on theoretical amount of sulfolene obtained, 471 grams.
$^c$Average of 2 tests.
$^d$Average of 3 tests.

EXAMPLE IV

This example illustrates that the presence of small amounts of dialkenyl amines does not affect the hydrogenation conversion of 3-sulfolene to sulfolane. To a 300 milliliter stainless steel reactor was charged 59 grams of recrystallized (from methyl alcohol) 3-sulfolene, 24 grams of water, 0.9 grams of Raney Nickel catalyst and 1.2 grams of diallylamine. The reactor was sealed, purged twice with hydrogen at 100 psig (689.47 kPa)/25° C., pressured to 500 psig (3447 kPa) and heated to about 43° C. for 2 hours. After cooling to about 25° C., the reactor was vented, purged with nitrogen and the contents filtered to remove catalyst. The filtrate was analyzed by GLC using a 4 foot column packed with 10% silicon rubber SE-30 on Chromosorb CP and programmed from 50° C. to 250° C. at a rate of 30° C. per minute. Analysis indicated 45.0 wt. % water, 1.4 wt. % amine and 53.5 wt. % sulfolane. The conversion from 3-sulfolene to sulfolane was 99+%. The run was repeated using various amounts of diallylamine plus a control where no diallylamine was present. These results listed in Table III show the conversion of 3-sulfolene to sulfolane is unaffected by the presence of small amounts of diallylamine.

TABLE III

Sulfolene Hydrogenation in the Presence of Diallylamine$^a$

| Sulfolene, g | H$_2$O g | Catalyst, g | Diallylamine g | Wt. % Amine | % Conversion |
|---|---|---|---|---|---|
| 50 | 50 | 1.13 | — | — | 99.4 |
| 59 | 24 | 0.9 | 0.6 | 1.0 | 99+ |
| 59 | 24 | 0.9 | 1.2 | 2.0 | 99+ |
| 59 | 24 | 0.9 | 1.8 | 3.0 | 99+ |
| 59 | 24 | 0.9 | 2.4 | 4.0 | 99+ |
| 59 | 24 | 0.9 | 3.0 | 5.0 | 99+ |

$^a$500 psig (3447 kPa) hydrogen, 43° C. 2 hours.

I claim:

1. A process for the production of a sulfolene which comprises reacting SO$_2$ and a conjugated diene in the presence of a small but effective amount, sufficient to minimize polymer formation, of an alkenyl amine of the formula

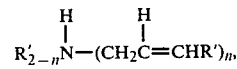

wherein n equals 1 or 2 and R' can be hydrogen or a hydrocarbyl radical having from 1 to 6 carbon atoms.

2. A process according to claim 1 wherein said diene has the structural formula

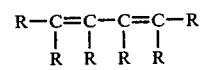

wherein each R is selected from the group consisting of hydrogen and organic and/or inorganic radicals which do not interfere with the reaction to produce the sulfolene compound.

3. A process according to claim 1 wherein the amount of alkenyl amine present ranges from about 0.01 to about 10 wt. % based on the amount of conjugated diene employed.

4. A process according to claim 1 which comprises the reaction of SO$_2$ with butadiene.

5. A process according to claim 4 wherein the alkenyl amine is diallylamine.

6. A process according to claim 1 further comprising contacting said sulfolene compound with hydrogen in the presence of a suitable hydrogenation catalyst under hydrogenation conditions to convert the sulfolene compound to the corresponding sulfolane compound.

7. A process according to claim 6 wherein said conjugated diene is butadiene, said amine is diallylamine, and said sulfolene compound is 2,3,4,5-tetrahydrothiophene-1,1-dioxide.

8. A process according to claim 6 wherein said alkenyl amine is diallylamine.

* * * * *